(12) United States Patent
Maxcy

(10) Patent No.: US 11,779,425 B2
(45) Date of Patent: Oct. 10, 2023

(54) SURGICAL MAT AND SURGICAL MARKING PEN TO PREVENT WRONG-SITE SURGERY

(71) Applicant: Colleen S. Maxcy, Tampa, FL (US)

(72) Inventor: Colleen S. Maxcy, Tampa, FL (US)

( * ) Notice: Subject to any disclaimer, the term of this patent is extended or adjusted under 35 U.S.C. 154(b) by 1134 days.

(21) Appl. No.: 16/460,819

(22) Filed: Jul. 2, 2019

(65) Prior Publication Data

US 2021/0000562 A1   Jan. 7, 2021

(51) Int. Cl.
| | | |
|---|---|---|
| *A61B 90/92* | (2016.01) | |
| *A61B 90/00* | (2016.01) | |
| *A47G 27/02* | (2006.01) | |
| *A61B 90/94* | (2016.01) | |
| *A41D 13/12* | (2006.01) | |
| *A41D 27/08* | (2006.01) | |

(52) U.S. Cl.
CPC .............. *A61B 90/08* (2016.02); *A47G 27/02* (2013.01); *A61B 90/92* (2016.02); *A41D 13/1236* (2013.01); *A41D 27/08* (2013.01); *A61B 90/94* (2016.02); *A61B 2090/0807* (2016.02); *A61B 2090/395* (2016.02)

(58) Field of Classification Search
CPC ......... A61B 17/22; A61B 5/411; A61B 50/30; A61B 90/08; A61B 90/39; A61B 90/94; A61B 2090/395; A61B 2090/3937; A61B 2090/0802; A61B 2090/0807; A61B 90/92; A41D 13/1236; A41D 27/08; A47G 9/0238; A47G 9/0246; A47G 27/02; A47G 27/023; A47G 27/0203
USPC ...... 227/19, 175.1, 156; 606/1, 139; 283/67, 283/74, 81; 482/23, 51, 71; 428/47, 50, 428/42, 156, 159, 160; 128/869, 897, 128/846, 853, 849
See application file for complete search history.

(56) References Cited

U.S. PATENT DOCUMENTS

| | | | | |
|---|---|---|---|---|
| 5,173,346 A | * | 12/1992 | Middleton | ................ B32B 5/18 4/581 |
| 5,357,861 A | * | 10/1994 | d'Arbelles | ............... B41K 1/54 101/406 |
| 6,286,682 B1 | * | 9/2001 | d'Arbelles | ............. A61B 90/39 206/572 |
| 6,293,916 B1 | * | 9/2001 | Alviso | ................... A61H 7/001 601/134 |

(Continued)

*Primary Examiner* — Scott A Smith
(74) *Attorney, Agent, or Firm* — Lewellyn Law, PLLC; Stephen Lewellyn

(57) ABSTRACT

A color-coded surgical table covering or floor mat and/or a surgical color-coded skin marker can be used in a medical setting to identify a bodily location of patient for which a medical procedure is to take place. The surgical color-coded skin marker may be used to mark the location of the medical procedure site on a patient. The medical patient would be oriented to match the surgical table covering or floor mat body form that identifies, through color and orientation, or text, the bodily location of a medical procedure to take place. The combination of the two (table covering/floor mat and skin marker) provides an unmistakable indication that will help limit or reduce wrong-site medical procedures. A surgical mat using a color-coded system or using visual indicia may be used to identify the medical procedure site to medical practitioners, in order to reduce wrong-site medical procedures.

5 Claims, 8 Drawing Sheets

(56) References Cited

U.S. PATENT DOCUMENTS

| | | | |
|---|---|---|---|
| 7,291,376 B1* | 11/2007 | Siegel | A47L 23/266 |
| | | | 428/167 |
| 8,192,330 B2 | 6/2012 | Curley | |
| 8,839,812 B2* | 9/2014 | Tanhehco | A61G 10/00 |
| | | | 604/356 |
| 9,721,064 B2 | 8/2017 | Khajavi | |
| 10,285,459 B2* | 5/2019 | Gubitosa | A41D 13/1236 |
| 2002/0179094 A1* | 12/2002 | Perlow | A61B 90/39 |
| | | | 128/897 |
| 2002/0187315 A1 | 12/2002 | Tanel | |
| 2003/0044561 A1 | 3/2003 | Kobayashi | |
| 2003/0184081 A1* | 10/2003 | Carlson, II | A61B 46/00 |
| | | | 283/67 |
| 2004/0056478 A1* | 3/2004 | Bruce | G09F 3/10 |
| | | | 283/81 |
| 2004/0229731 A1 | 11/2004 | Mitchell | |
| 2006/0086026 A1* | 4/2006 | Ho | G09F 19/22 |
| | | | 40/618 |
| 2007/0088232 A1 | 4/2007 | Corradini | |
| 2007/0173356 A1 | 7/2007 | Hapanowicz | |
| 2008/0033405 A1* | 2/2008 | Hered | A61B 90/39 |
| | | | 606/1 |
| 2008/0196144 A1* | 8/2008 | Ruiz | A41D 13/1236 |
| | | | 2/171 |
| 2014/0329044 A1 | 11/2014 | Fantin | |
| 2016/0081405 A1 | 3/2016 | Gubitosa | |
| 2019/0117039 A1 | 4/2019 | McKeown | |

* cited by examiner

SURGICAL MAT AND SURGICAL MARKING PEN TO PREVENT WRONG-SITE SURGERY

BACKGROUND

"Wrong-site, wrong-procedure, wrong-patient errors" (WSPEs) occur but should not happen. WSPEs surgery is generally defined as an operation or medical procedure performed on the wrong part of the body of a medical patient. Under this definition, there are a number of types of wrong site medical procedures involving surgeries. For example, WSPEs surgery may include surgery performed on the incorrect side of a body of a medical patient, surgery performed on the correct side of the body of a medical patient but at the wrong site (body area). It may also include an incorrect operation performed on the correct side and correct location of the medical patient and a procedure or operation performed correctly but on the wrong medical patient.

Some estimate that as many as 50 WSPEs surgeries occur each week in the United States alone, however, there is limited information as to the exact number of such occurrences due to underreporting by doctors and hospitals. Regardless, this is a serious matter than can have disastrous outcomes including permanent disfigurement or even the death of a medical patient.

Statistics show that medical errors are the eighth leading cause of death in the United States, accounting for 44,000 to 98,000 deaths each year. The measurable costs associated with medical errors are estimated to cost Americans nearly $37.6 billion per year. Non-measurable costs include loss of trust in the medical profession; diminished patient satisfaction; physical and psychological discomfort to the patient and the patient's family; and lower morale and increased frustration on the part of medical practitioners themselves. Of these costs, nearly $17 billion per year are believed to be preventable. Prevention of these errors would naturally yield a commensurate positive impact on the non-measurable costs as well.

Some of these errors are attributable to communication breakdown; documentation errors; X-rays that are mislabeled, misread, and/or positioned incorrectly; chart errors; fatigue; impaired memory; pressure; and a lack of surgical site verification. The lack of surgical site verification often results in the occurrence of surgery being performed in incorrect locations. Moreover, it has been found that there is a statistically higher risk of incorrect or wrong-site surgery being performed in bilateral surgeries such as orthopedic surgery and the like.

As such, there have been numerous attempts to remedy the frequency of these occurrences, but these attempts have resulted in little to no impact on the number of such incidents. One such remedy is to have the medical patient and physician mark the site to be subjected to a medical procedure. Another potential remedy involves thorough checklist(s) with a planned "time out" that occurs before the surgery or medical procedure. In this "time out" period, the name, charts, and surgery site (amongst other variables) of the medical patient are to be reviewed. However, these checklists are often only partially performed or performed incorrectly by the medical practitioners.

One major problem plaguing surgical rooms and exacerbating the number of wrong site medical procedures is the lack of a universal standard for prevention of such occurrences. Currently, different medical facilities and establishments follow similar, but not identical guidelines. Further, as mentioned above, there are often breakdowns in these processes. In some instances, time constraints result in rushed or incomplete medical patient assessments and the aforementioned "time outs." Additionally, similar medical patient names, short hand notation used by hospital staff, and the involvement of multiple individuals all contribute to the lack of cohesion that can result in a WSPEs surgery or other incorrect medical procedure.

Thus, there is a need for a simple, yet effective, solution to drastically limit or prevent wrong site surgeries. Such a solution should further be cost-effective and relatively straightforward and readily understandable in nature in order to enable any medical facility or establishment to easily implement the changes necessary to meet these needs. The present invention and its aspects meet and exceed these objectives.

SUMMARY

In a first aspect of the invention, the invention provides a medical procedure site identification kit, including at least one surgical mat and at least one color-coded surgical marker. The mat has at least one color that indicates a medical procedure site or a neutral site, and the marker has a first marking color that is the same color as the at least one color of the mat.

In a second aspect of the invention, the invention provides a method of identifying a medical procedure site. The method includes selecting a surgical mat and a surgical marker combination, marking a location of a medical procedure site on a medical patient's body using the surgical marker; and placing the mat adjacent to an operating room table. The surgical mat has at least one color that indicates a medical procedure site or a neutral site, and the marker has a first marking color that corresponds to the at least one color of the mat that indicates the medical procedure site or the neutral site.

In a third aspect, the present invention provides a method of identifying a medical procedure site, including choosing a surgical mat that includes at least one color or visual indicium that corresponds to a location of a medical procedure site from a selection of surgical mats, placing the mat adjacent to an operating room table, and performing an operation on a patient at the location indicated by the surgical mat.

DEFINITIONS

As used herein a "medical procedure site" is a location on a body, preferably human, that is subject to an invasive or non-invasive medical procedure to be performed with the intent of determining, measuring, diagnosing, or treating a condition associated with a subject or medical patient.

As used herein a "neutral site" is a location on a body, preferably human, that is not subject to an invasive or non-invasive medical procedure to be performed with the intent of determining, measuring, diagnosing, or treating a condition associated with a subject or medical patient.

As used herein, "visual indicia" or "visual indicium" refers to the symbols, characters, words or phrases used to indicate the neutral site or the medical procedure site for a medical procedure.

DETAILED DESCRIPTION

Figure 1A:
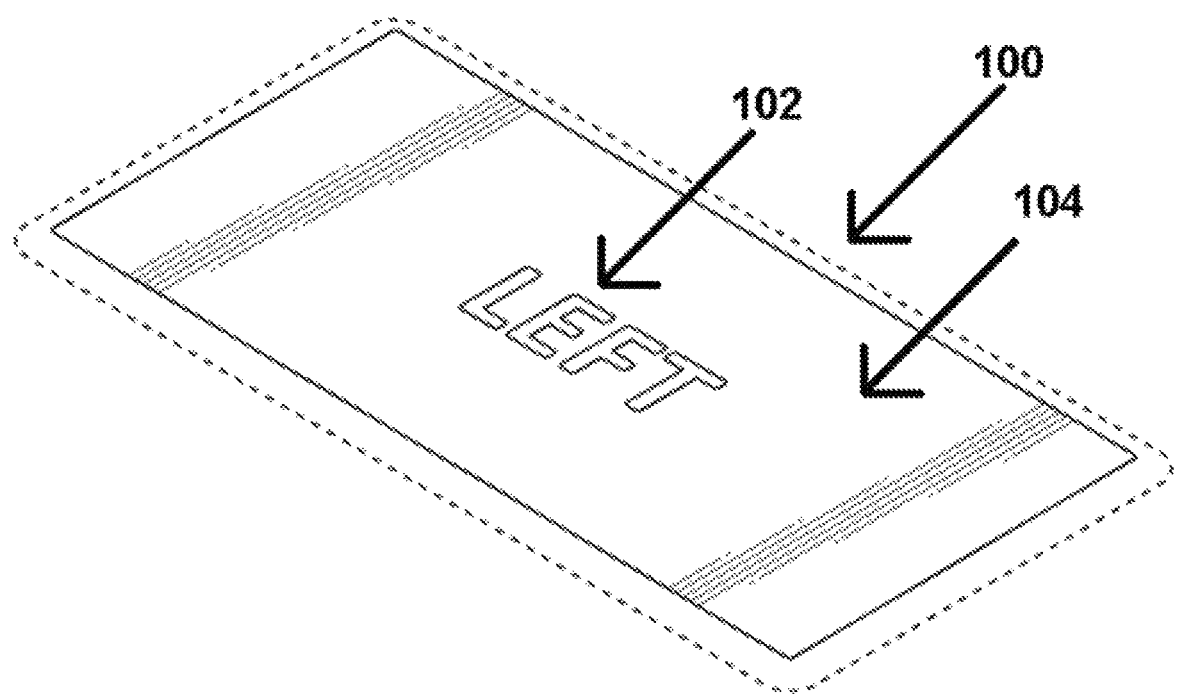
FIG. 1A is a plan view of a surgical mat with the word "LEFT" shown on the top surface.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including." and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred aspects of this invention are described herein, including the best mode known to the inventors for carrying out the invention. Variations of those preferred aspects may become apparent to those of ordinary skill in the art upon reading the description herein. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

A medical procedure site identification kit is described, which includes a surgical mat and a color-coded surgical marker. The surgical marker may be used to mark the medical procedure site location on a patient's body with a first marking color that indicates that the marked location is the medical procedure site. The surgical mat may be selected to indicate the medical procedure site location, and the surgical mat may have a color that corresponds to the first marking color which is used to mark the location of the medical procedure site. The surgical mat may also include a visual indicium on the surface that indicates the location of the medical procedure site. The visual indicia may be any form of warning including characters, words, images and the like or any combination thereof. For example, the surgical mat may have a visual indicium of the word "LEFT", which indicates the left side is the correct medical procedure site, or the word "BILATERAL" or "CENTRAL", which indicates the medical procedure site is located centrally or in a bilateral location on the patient. Also, color can be used to indicate the location of the medical procedure site.

An aspect includes a method of identifying a medical procedure site using a color-coded system, which makes use of a surgical mat and a color-coded surgical marker. This method may include using a surgical marker to mark the medical procedure site and/or a neutral site on a patient, where the color of the marker corresponds to the color-coding system of the surgical mat. The color-coding system includes at least two colors. For example, red may signify to the medical practitioner to operate on the right side of the body, thus alerting the medical practitioner that this side is subject to a medical procedure. A contrasting color, such as blue or green, may be used to signify the left side of the body as the medical procedure site. Visual indicia may be used in conjunction with the color-coding system.

Another aspect describes a method of identifying a medical procedure site by positioning a surgical mat adjacent to an operating room table, where the mat has a color and/or visual indicium that indicates the location of the medical procedure site. A preferred color-coding system uses the color red to indicate to the medical practitioner that the medical procedure site is on the right side of the patient's body. For example, a red mat may indicate the medical procedure site is on the right side of the patient's body, a blue mat may indicate that the medical procedure site is on the left side of the patient's body, and a black mat may indicate that the medical procedure site is central or bilateral to the patient's body. In addition to the color, the surgical mat may also include a visual indicium such as the word "RIGHT", "LEFT", "CENTRAL", or "BILATERAL" (or their non-English equivalents). The surgical mat may also include patterns to indicate that the medical procedure site is on the left or right side of a patient's body. For example, a diamond pattern may indicate that the medical procedure site is on the right side of the patient's body, and a pinstripe pattern may indicate that the medical procedure site is on the left side of the patient's body. The surgical marker may also include patterns that correspond to the color of the marking color. These patterns allow a medical practitioner who is color-blind to visually determine the correct medical procedure site location.

Referring now to FIG. 1A, there is a color-coded surgical mat 100 displaying a color scheme. The surgical mat 100 as shown has a color identification system, however, other symbols, characters, words, phrases and the like may be used singularly or in any combination. In FIG. 1A, the visual indicium 102 is the word "LEFT". The color 104 of the mat may be any color selected to correspond to a neutral site or a medical procedure site. In the preferred color-coding system, the color blue is associated with a medical procedure site on the left side of the patient's body.

Figure 1B:
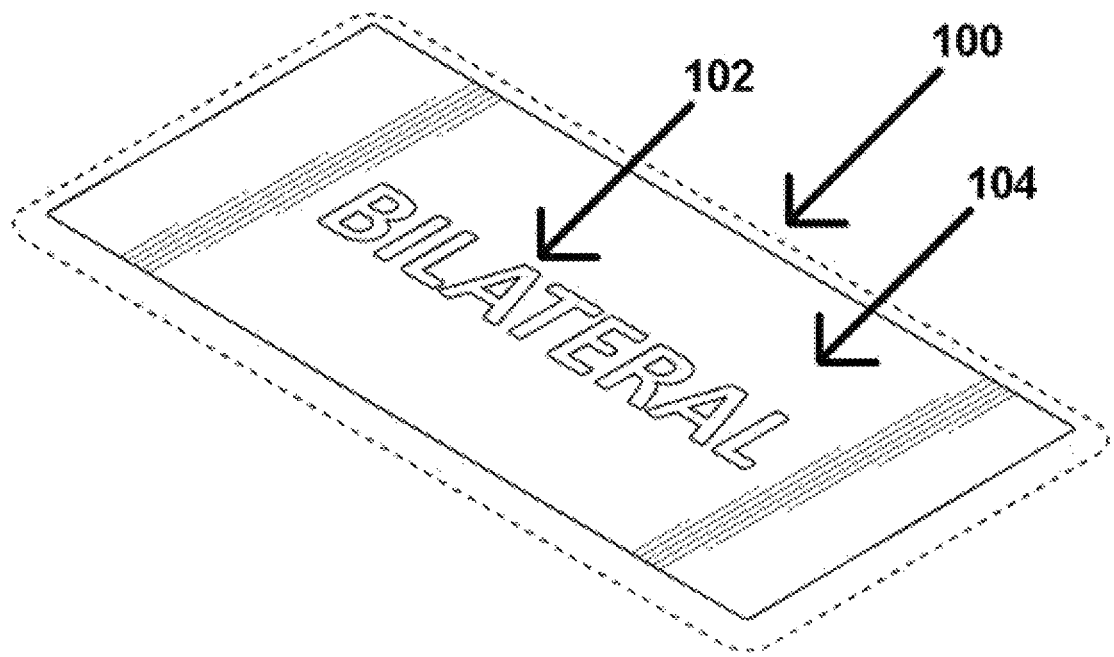
FIG. 1B is a plan view of surgical mat with the word "BILATERAL" shown on the top of the mat.

FIG. 1B illustrates a color-coded surgical mat 100 displaying a visual indicium 102 for use when the medical procedure site is a bilateral location. The visual indicia in FIG. 1B is the word "BILATERAL". The color 104 of the mat is preferably black. In the preferred color-coding system, the color black is preferably used to indicate that the medical procedure site is a bilateral location.

Figure 1C:
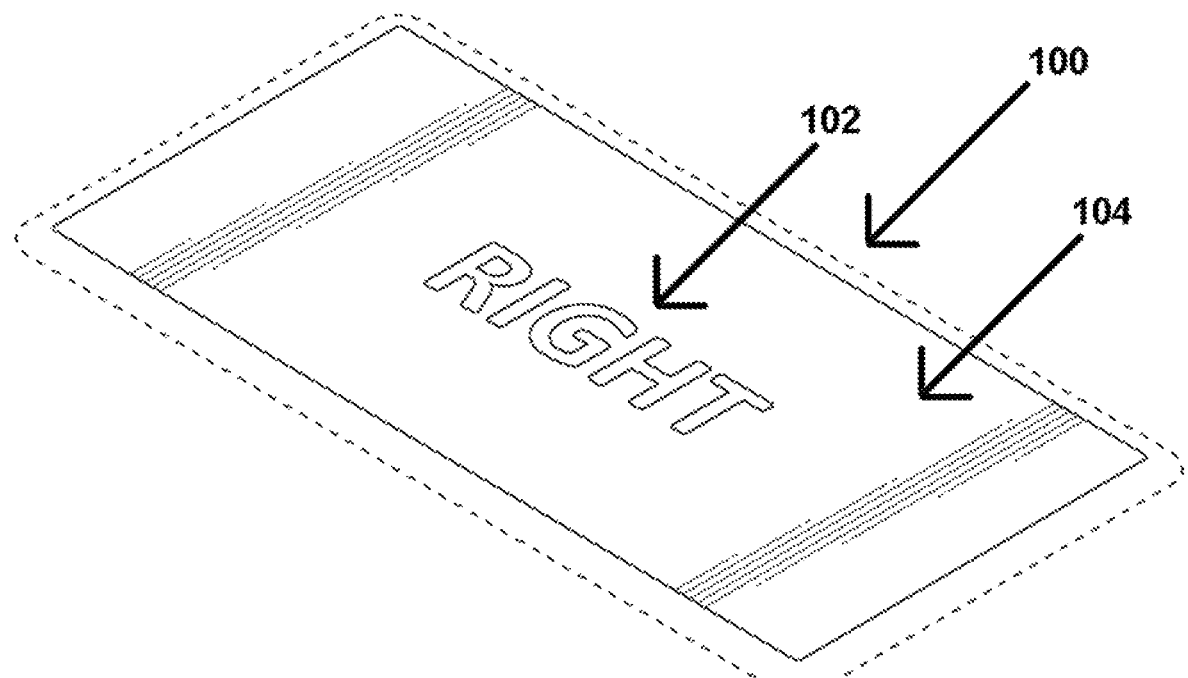
FIG. 1C is a plan view of surgical mat with the word "RIGHT" shown on the top of the mat.

FIG. 1C illustrates a color-coded surgical mat 100 displaying a color scheme. The surgical mat 100 as shown has a color identification system, however, other symbols, characters, words, phrases and the like may be used singularly or in any combination. The visual indicia in FIG. 1C is the word "RIGHT". The color 104 of the mat is preferably red. In the preferred color-coding system, the color red is preferably used to indicate that the medical procedure site is on the right side of the patient's body.

Figure 2:
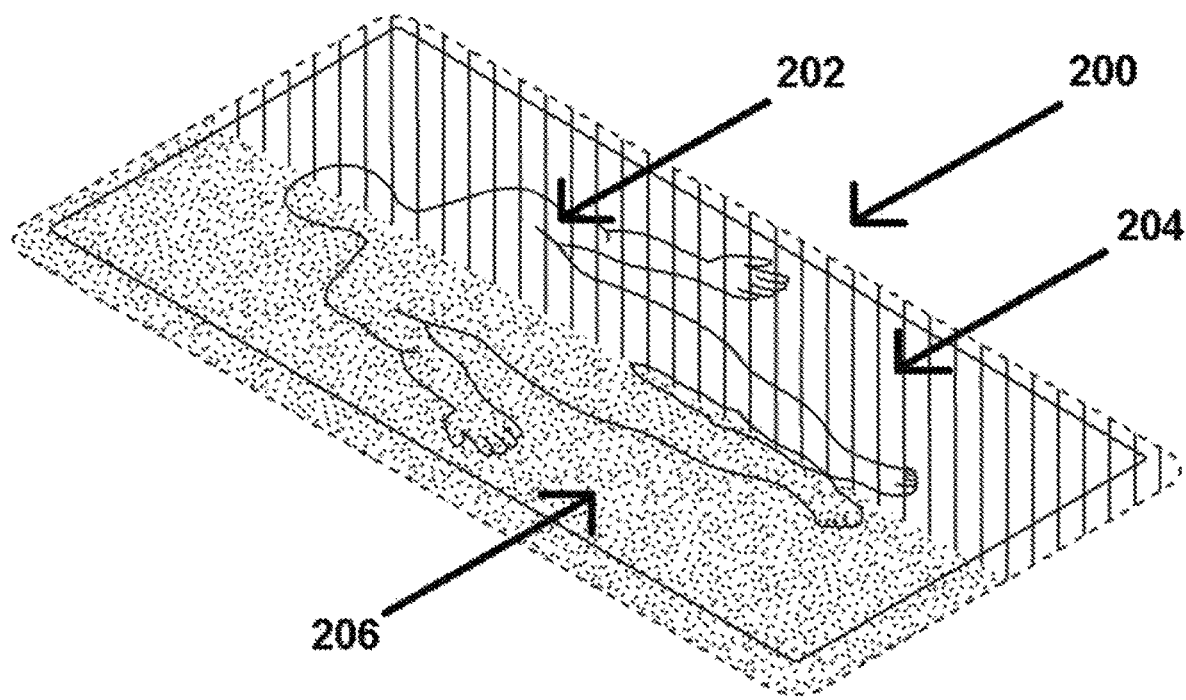
FIG. 2 is a plan view of a surgical mat showing a human figure with a first color and a second contrasting color.

In another aspect, the color identification system preferably has at least two colors. FIG. 2 illustrates a color-coded surgical mat 200 having two colors. The surgical mat has an outline of a human FIG. 202, a first color 204, and a second color 206. The two colors are used to determine the side of a body, either left or right, that is subject to a medical procedure. The first color should be distinct and in contrast to second color. Further, surgical mat may also include at least one visual indicium to indicate the relative position, for example, "RIGHT" and/or "LEFT".

In some aspects, a first color is a color that signifies the side of the body that is a neutral site. As such, the color used is preferably red to inform the medical practitioner to stop, thus alerting any individual that the side is not subject to a medical procedure. Also, a second color is a color that signifies that side of the body is subject to a medical procedure. As such, the color used is preferably green to signify the medical procedure site.

Figure 3A:
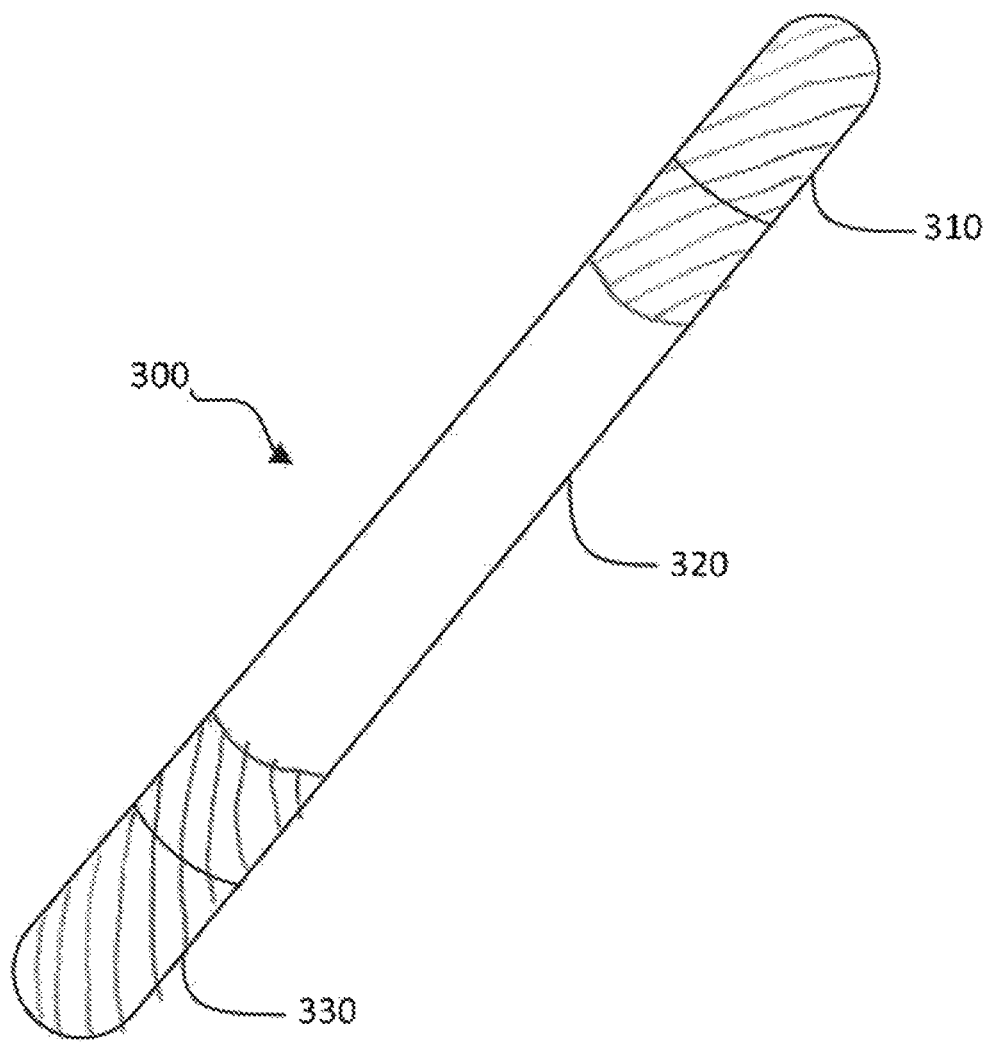
FIG. 3A is a perspective view of a dual-end surgical pen of an aspect.
Figure 3B:
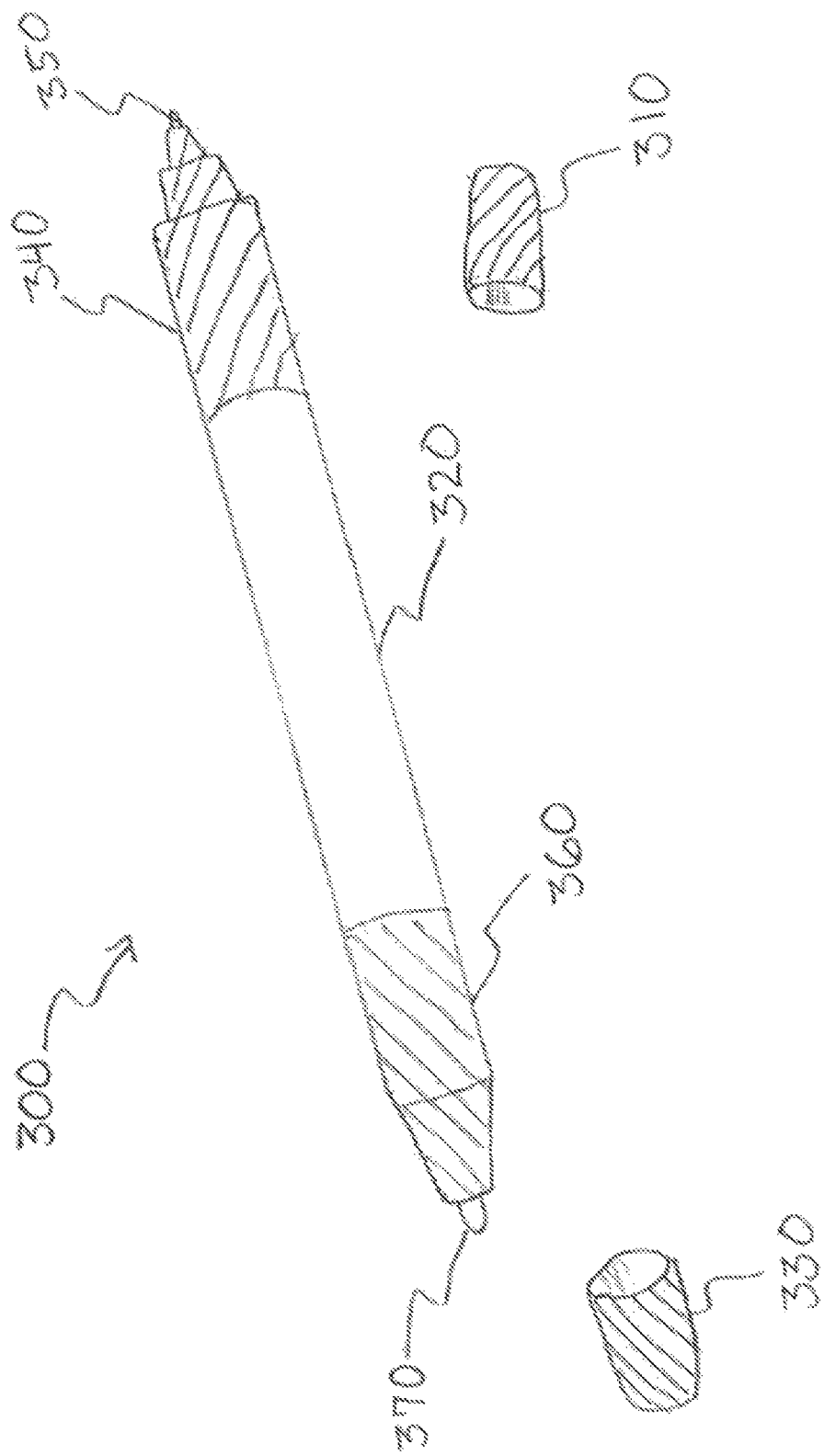
FIG. 3B is an expanded view of the surgical pen of FIG. 3A.

Referring now to FIGS. 3A and 3B, there is at least one color-coded surgical marker 300 displaying multiple color schemes and combinations of such schemes. Generally, the marker 300 as shown has a color identification system, however, other symbols, characters, words, phrases and the like may be used singularly or in any combination. In some aspects, the color identification system is used to signify the location of a medical procedure and the location of a neutral site or non-medical procedure site. The marker ink should be easily visible on any skin type. In certain aspects, the ink is a medical-grade, non-irritating gentian ink disposed in marker 300.

Surgical marker 300 may include a set of surgical markers of differing colors according to the color identification system described herein. For simplification purposes FIGS. 3A and 3B show at least one color-coded surgical marker 300. Surgical marker 300 includes a dual end (340, 360).

FIG. 3A illustrates a perspective view of surgical marker 300 has a marker body 320 and a removable first color-coded marker cap 310 and a removable second color-coded marker cap 330. The dual end (340, 360) may be colorized to indicate an ink color to be used during a medical procedure site procedure. The surgical marker may include patterns that indicate the marking color. The pattern may be present on the marker body or the color-coded marker caps. For example, the first color-coded marker cap has a red color and a diamond pattern, and the second color-coded marker cap has a blue color and a pinstripe pattern.

FIG. 3B illustrates an expanded view of surgical marker 300 showing the removable color-coded marker caps (310, 330) exposing a first color marker writing tip 350 and a second color marker writing tip 370. The first color marking writing tip 350 differs from the second color marker writing tip 370. In some aspects, writing tip 350, cap 310 and first color-coded end 340 are the same color. Further, writing tip 370, cap 330 and second color-coded end 360 are the same color. These differing marker colors are configured to match the color scheme of a surgical mat 200 to indicate a medical procedure site and a neutral site in preferred aspects. Further, the at least one color-coded surgical marker 300 may be sterile for operating room use. Also, surgical marker 300 may have a cylindrical or a triangular transverse profile.

Surgical marker 300 is used to mark the medical procedure site on the patient in combination with the surgical mat 200 to coincide with the correct color scheme and medical procedure site for the medical patient. Thus, the patient orientation relative to the human FIG. 202, and matching color-coding scheme provide a clear and concise checkpoint system for a nurse, a doctor, or other medical practitioner to confirm the medical procedure site.

The surgical mat may be the floor mats sold by GELPRO®, such as the ELITE™ floor mat. The surgical mat may also be produced of similar materials and have similar dimensions as the ELITE™ floor mat. The surgical mat may have a non-slip bottom, in order to avoid unwanted movement, and the surgical mat may include memory foam to reduce fatigue from standing during lengthy medical procedures. Preferably the mat has tapered edges to avoid the risk of tripping on the mat. In some aspects, surgical mats may be a surgical cover or operating room table cover to lie a patient upon prior to a medical procedure. Further, surgical mats may be sterile for operating room use.

Figure 4:
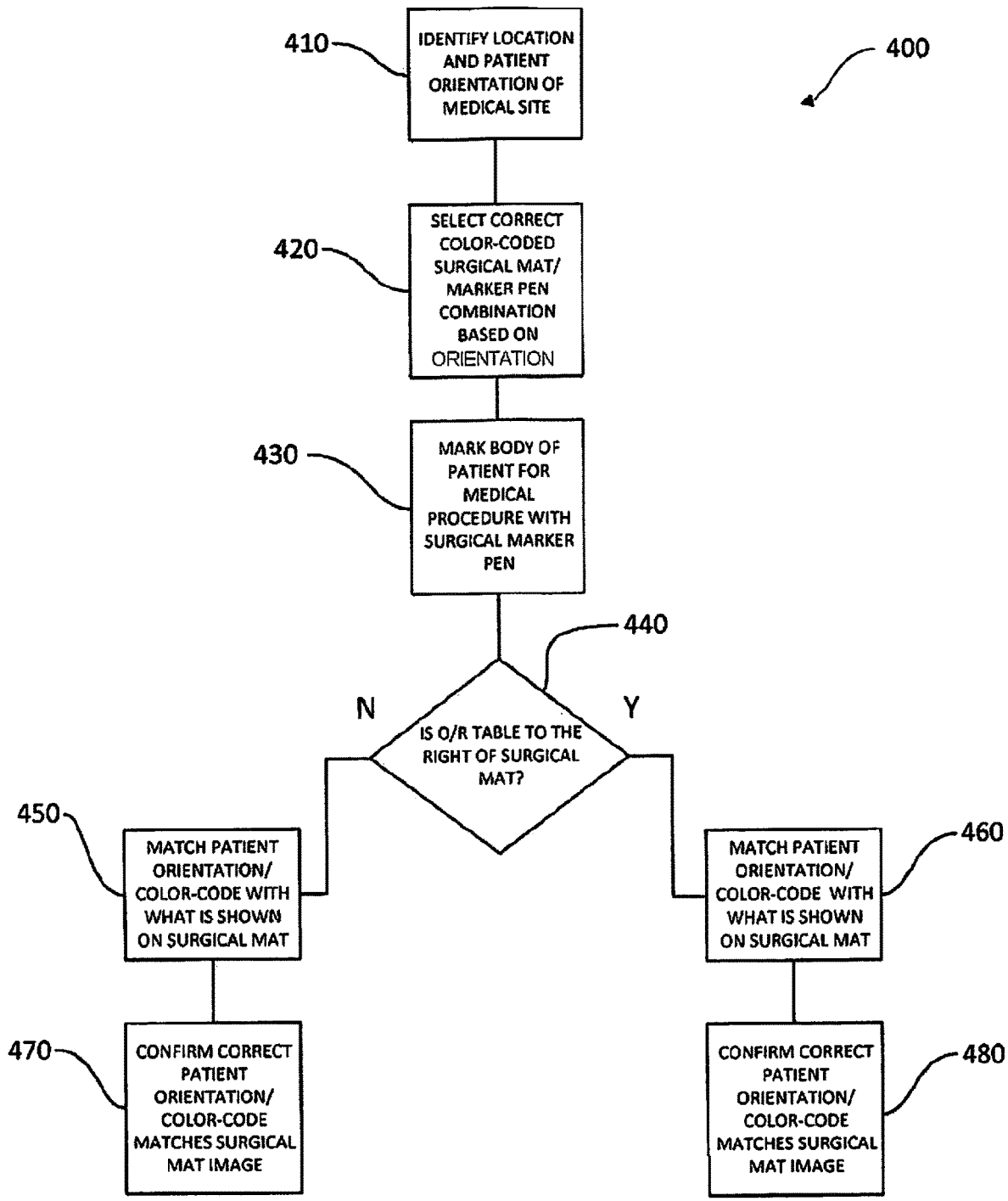
FIG. 4 is a flowchart of a method of implementing an aspect.

Referring to FIG. 4, there is a flowchart illustrating a method 400 of verifying that the correct surgical mat and surgical marker 300 color-coded end (340, 360), as shown in FIGS. 2-3B, are used to correctly identify a site of a medical procedure to take place on a medical patient's body.

Often, a medical patient, when arriving at a medical facility such as a hospital or surgical center, the medical patient must first check in. This verifies the medical patient is at the facility and the facility can begin the prepping phase. Normally a nurse or practitioner will come out after to meet and greet the patient and take them to begin the pre-procedure prepping process.

At 410, the medical practitioner identifies (verifies) the side of the medical patient's body for the medical procedure to take place. The nurse or practitioner may ask the patient which side of the body is the medical procedure to be performed and compare the medical patient's response with their medical records.

At 420, the correct color-coded surgical mat and marker combination is selected. The medical practitioner may provide the medical patient with a variety of prepackaged surgical mat and marker combinations asking the medical patient to confirm the correct mat/marker combination.

There may be numerous combinations of mat/marker but exemplary combinations should be right side medical procedure, left side medical procedure, right side prone medical procedure, and left side prone medical procedure or any combination thereof. The medical practitioner may also have to inform the medical patient whether they will be placed in a supine or prone position. The medical practitioner and/or patient should then select and/or confirm a mat/marker combination package and the medical practitioner should then verify that the correct combination has been selected.

At 430, the patient's body is marked by the medical practitioner with the color-coded surgical marker 300 at the proper medical procedure site based on the confirmed combination chosen by the patient and/or practitioner according to the color-coded identification system.

At 440, the correct surgical mat is determined and confirmed relative to the OR table position to the patient's required orientation for their medical procedure(s).

At 450 or 460, once the patient has been marked and oriented for the color-coded identification system, both the medical patient and the medical practitioner verify the surgical mat is on in the correct orientation and the correct marker color has been selected for the procedural and/or neutral sites. The medical practitioner can then verify and sign off on the verification of the proper mat selection. The medical patient may then be asked to do the same. The medical practitioner can then have the patient lie down in the correct position on the operating room table.

At 470 or 480, the medical practitioner can observe, as well as the medical patient, whether the color scheme of the mat and the marked medical procedural area align with one another. It should be visually apparent that the colors on each side of the midline of the mat and the marker color align and match one another. If this is not the case, the method 400 should be restarted to ensure accuracy. Once the medical procedure is to begin, the staff will still perform any and all other protocol including "time out" procedures to further ensure the medical patient's identity, the medical procedure to be performed, and the nature of the medical procedure.

After confirming the correct medical procedure site, the medical practitioner will carry out the medical procedure on the appropriate medical procedure site. The procedure may be a surgery or operation. The procedure may be carried out by a surgeon. A nurse or other medical practitioner may assist in the surgery. The medical practitioner may stand on the mat for periods of time during the procedure to reduce fatigue.

Figure 5:
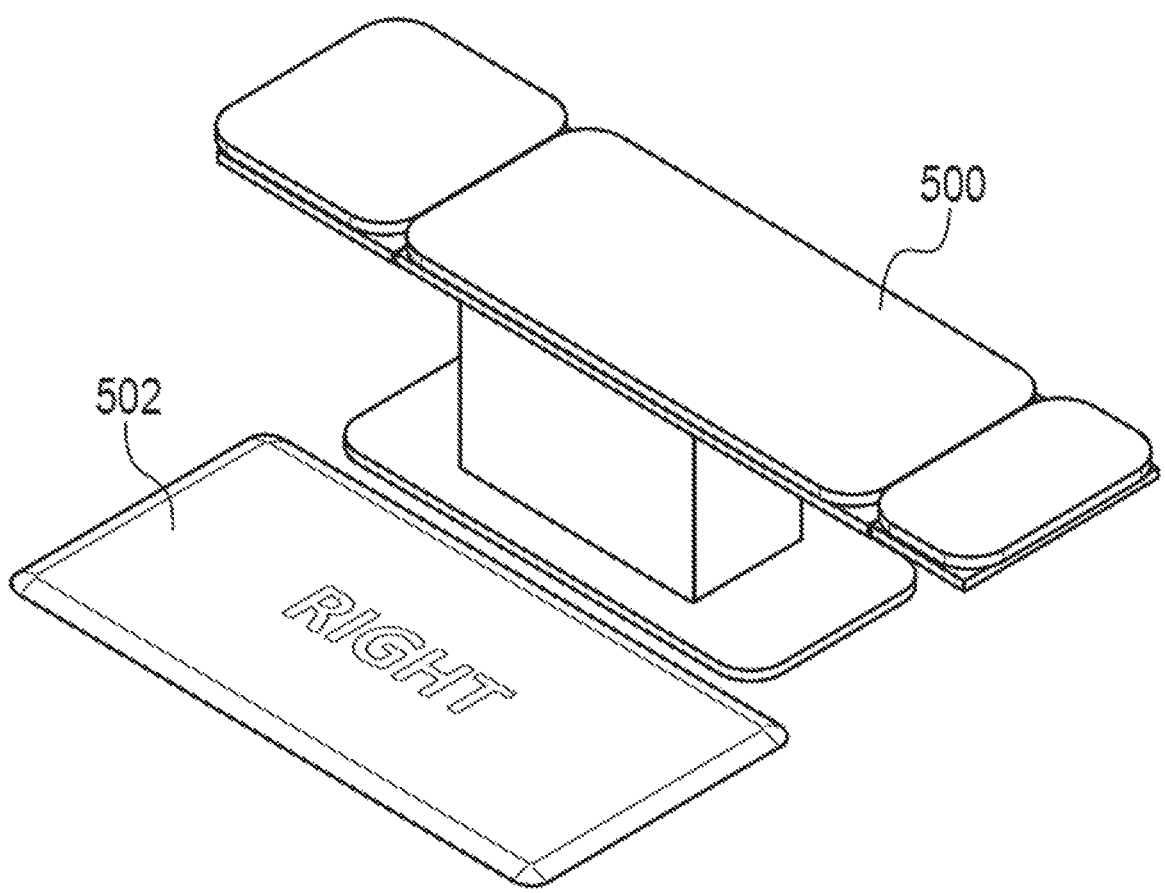
FIG. 5 illustrates an operating room table and a surgical mat.

FIG. 5 illustrates an operating room table 500. A surgical mat 502 may be placed adjacent to the operating room table, in a location that is next to and parallel to the operating room table. The mat may have a color or visual indicia to indicate the medical procedure site is on the left, right, or center portion of a patient's body. The color or visual indicia may be any of the colors or indicia described herein.

The surgical floor mats described in U.S. application Ser. No. 29/691,863 are hereby incorporated by reference.

What is claimed is:

1. A method of preventing wrong-site surgery, the method comprising the steps of:
   selecting a surgical floor mat having a mat color;
   marking a medical procedure site location on a patient's body using a surgical marker of a marking color that matches the mat color;
   placing the surgical floor mat on a floor surface that is adjacent to an operating room table upon which the patient is placed and on a side of the operating room table corresponding to the medical procedure site location marked on the patient's body and an orientation of the patient on the operating room table; and
   standing on the surgical floor mat and visually inspecting the mat color against the marking color to determine if the mat color and marking color match before conducting a medical procedure on the patient.

2. The method of claim 1, wherein the surgical mat comprises at least one visual indicium.

3. The method of claim 2, wherein the visual indicia comprise the word "RIGHT" or the word "LEFT".

4. A method of preventing wrong-site surgery, the method comprising the steps of:
   selecting a first a surgical floor mat having a first mat color and a second surgical floor mat having a second mat color;
   marking a medical procedure site location on a patient's body using a surgical marker of a first marking color that matches the first mat color;
   marking a neutral site location on a patient's body using a surgical marker of a second marking color that matches the second mat color;
   placing the first surgical floor mat on a floor surface that is adjacent to an operating room table upon which the patient is placed and on a side of the operating room table corresponding to the medical procedure site location marked on the patient's body and an orientation of the patient on the operating room table; and
   placing the second surgical floor mat on a floor surface that is adjacent to an operating room table upon which the patient is placed and on a side of the operating room table corresponding to the neutral site location marked on the patient's body and the orientation of the patient on the operating room table.

5. The method of claim 4 further comprising the step of:
   standing on first the surgical floor mat and visually inspecting the first mat color against the first marking color to determine if the first mat color and first marking color match before conducting a medical procedure on the patient.

* * * * *